US010266898B2

(12) United States Patent
Kim et al.

(10) Patent No.: US 10,266,898 B2
(45) Date of Patent: Apr. 23, 2019

(54) COMPOSITION FOR DIAGNOSING RECURRING GLIOBLASTOMA MULTIFORME AND METHOD FOR DIAGNOSING SAME

(71) Applicant: Korea Basic Science Institute, Daejeon (KR)

(72) Inventors: Gun-Hwa Kim, Daejeon (KR); Giwon Kim, Daejeon (KR); Soohyun Kim, Daejeon (KR); Seung Il Kim, Daejeon (KR); Edmond Changkyun Park, Daejeon (KR)

(73) Assignee: KOREA BASIC SCIENCE INSTITUTE, Daejeon (KR)

(*) Notice: Subject to any disclaimer, the term of this patent is extended or adjusted under 35 U.S.C. 154(b) by 51 days.

(21) Appl. No.: 14/600,419

(22) Filed: Jan. 20, 2015

(65) Prior Publication Data
US 2015/0232946 A1 Aug. 20, 2015

Related U.S. Application Data

(63) Continuation of application No. PCT/KR2013/006519, filed on Jul. 22, 2013.

(30) Foreign Application Priority Data

Jul. 20, 2012 (KR) .................. 10-2012-0079314

(51) Int. Cl.
*C12Q 1/68* (2018.01)
*C12P 19/34* (2006.01)
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/16* (2013.01); *C12Q 2600/178* (2013.01)

(58) Field of Classification Search
CPC ........... C12Q 1/6886; C12Q 2600/158; C12Q 2600/178
See application file for complete search history.

(56) References Cited

U.S. PATENT DOCUMENTS

2011/0301221 A1* 12/2011 Lin ................... C12Q 1/6886
514/44 A

OTHER PUBLICATIONS

Cheung, V.G. et al. Nature Genetics (Mar. 2003) vol. 33, pp. 422-425.*
Hoshikawa Y. et al. Physiol Genomics 12: 209-219, 2003.*
Cobb, J.P. et al. Crit Care Med 2002 vol. 30, No. 12.*
Kim G. et al. Journal of Analytical Science & Technology (2011) 2 (2), 97-104.*
Ujifuku K. et al. Cancer Letters 296 (2010) 241-248.*
GenBank Locus: HC885758 "Sequence 13 from Patent WO2010055488" (Jun. 10, 2010), from www.ncbi.nlm.nih.gov/nuccore/HC885758.1*
Silber J. et al. BMC Medicine 2008, 6:14, pp. 1-17.*
"TaqMan Array Human MicroRNA Cards", two printed pages from http://www3.appliedbiosystems.com/cms/groups/mcb_marketing/documents/generaldocuments/cms_054742.pdf (Year: 2010).*
"TaqMan MicroRNA Assays and Arrays" four printed pages from http://www3.appliedbiosystems.com/cms/groups/mcb_marketing/documents/generaldocuments/cms_042142.pdf (Year: 2011).*

* cited by examiner

*Primary Examiner* — Stephen T Kapushoc
(74) *Attorney, Agent, or Firm* — Sughrue Mion, PLLC

(57) ABSTRACT

The present invention relates to a recurring glioblastoma multiforme marker miRNA for diagnosing recurring glioblastoma multiforme, and more specifically, to a composition for screening the miRNA marker, which is specific to the recurring glioblastoma multiforme and comprises an agent for detecting the presence of the marker, a kit, and to a method for diagnosing the recurring glioblastoma multiforme using same. The method for diagnosing the recurring glioblastoma multiforme by using the recurring glioblastoma multiforme marker miRNA, according to the present invention, provides glioblastoma markers, which can diagnose the occurrence of the recurring glioblastoma multiforme, thereby providing useful material for managing treatment and prognosis of the recurring glioblastoma multiforme. In addition, the diagnosis markers for the recurring glioblastoma multiforme can be used for development and research of an anticancer agent specific to the recurring glioblastoma multiforme.

5 Claims, 4 Drawing Sheets
Specification includes a Sequence Listing.

SEQUENCE LISTING

<160> NUMBER OF SEQ ID NOS: 37

<210> SEQ ID NO 1
<211> LENGTH: 21
<212> TYPE: DNA
<213> ORGANISM: Artificial Sequence
<220> FEATURE:
<223> OTHER INFORMATION: hsa-miR-365

<400> SEQUENCE: 1
taatgcccct aaaaatcctt a                                          21

<210> SEQ ID NO 2
<211> LENGTH: 23
<212> TYPE: DNA
<213> ORGANISM: Artificial Sequence
<220> FEATURE:
<223> OTHER INFORMATION: hsa-miR-29b

<400> SEQUENCE: 2
tagcaccatt tgaaatcagt gtt                                        23

<210> SEQ ID NO 3
<211> LENGTH: 23
<212> TYPE: DNA
<213> ORGANISM: Artificial Sequence
<220> FEATURE:
<223> OTHER INFORMATION: hsa-miR-34c-5p

<400> SEQUENCE: 3
aggcagtgta gttagctgat tgc                                        23

<210> SEQ ID NO 4
<211> LENGTH: 22
<212> TYPE: DNA
<213> ORGANISM: Artificial Sequence
<220> FEATURE:
<223> OTHER INFORMATION: hsa-miR-129-3p

<400> SEQUENCE: 4
aagcccttac cccaaaaagc at                                         22

<210> SEQ ID NO 5
<211> LENGTH: 21
<212> TYPE: DNA
<213> ORGANISM: Artificial Sequence
<220> FEATURE:
<223> OTHER INFORMATION: hsa-miR-218

<400> SEQUENCE: 5
ttgtgcttga tctaaccatg t                                          21

<210> SEQ ID NO 6
<211> LENGTH: 20
<212> TYPE: DNA
<213> ORGANISM: Artificial Sequence
<220> FEATURE:
<223> OTHER INFORMATION: hsa-miR-124

<400> SEQUENCE: 6
taaggcacgc ggtgaatgcc                                            20

<210> SEQ ID NO 7
<211> LENGTH: 22
<212> TYPE: DNA
<213> ORGANISM: Artificial Sequence

```
<220> FEATURE:
<223> OTHER INFORMATION: hsa-miR-486-5p

<400> SEQUENCE: 7
tcctgtactg agctgccccg ag                                         22

<210> SEQ ID NO 8
<211> LENGTH: 23
<212> TYPE: DNA
<213> ORGANISM: Artificial Sequence
<220> FEATURE:
<223> OTHER INFORMATION: hsa-miR-10b

<400> SEQUENCE: 8
taccctgtag aaccgaattt gtg                                        23

<210> SEQ ID NO 9
<211> LENGTH: 22
<212> TYPE: DNA
<213> ORGANISM: Artificial Sequence
<220> FEATURE:
<223> OTHER INFORMATION: hsa-miR-95

<400> SEQUENCE: 9
ttcaacgggt atttattgag ca                                         22

<210> SEQ ID NO 10
<211> LENGTH: 22
<212> TYPE: DNA
<213> ORGANISM: Artificial Sequence
<220> FEATURE:
<223> OTHER INFORMATION: hsa-miR-154

<400> SEQUENCE: 10
taggttatcc gtgttgcctt cg                                         22

<210> SEQ ID NO 11
<211> LENGTH: 21
<212> TYPE: DNA
<213> ORGANISM: Artificial Sequence
<220> FEATURE:
<223> OTHER INFORMATION: hsa-miR-224

<400> SEQUENCE: 11
caagtcacta gtggttccgt t                                          21

<210> SEQ ID NO 12
<211> LENGTH: 22
<212> TYPE: DNA
<213> ORGANISM: Artificial Sequence
<220> FEATURE:
<223> OTHER INFORMATION: hsa-miR-299-3p

<400> SEQUENCE: 12
tatgtgggat ggtaaaccgc tt                                         22

<210> SEQ ID NO 13
<211> LENGTH: 22
<212> TYPE: DNA
<213> ORGANISM: Artificial Sequence
<220> FEATURE:
<223> OTHER INFORMATION: hsa-miR-299-5p

<400> SEQUENCE: 13
tggtttaccg tcccacatac at                                         22
```

```
<210> SEQ ID NO 14
<211> LENGTH: 21
<212> TYPE: DNA
<213> ORGANISM: Artificial Sequence
<220> FEATURE:
<223> OTHER INFORMATION: hsa-miR-376a

<400> SEQUENCE: 14
atcatagagg aaaatccacg t                                              21

<210> SEQ ID NO 15
<211> LENGTH: 21
<212> TYPE: DNA
<213> ORGANISM: Artificial Sequence
<220> FEATURE:
<223> OTHER INFORMATION: hsa-miR-376c

<400> SEQUENCE: 15
aacatagagg aaattccacg t                                              21

<210> SEQ ID NO 16
<211> LENGTH: 21
<212> TYPE: DNA
<213> ORGANISM: Artificial Sequence
<220> FEATURE:
<223> OTHER INFORMATION: hsa-miR-379

<400> SEQUENCE: 16
tggtagacta tggaacgtag g                                              21

<210> SEQ ID NO 17
<211> LENGTH: 21
<212> TYPE: DNA
<213> ORGANISM: Artificial Sequence
<220> FEATURE:
<223> OTHER INFORMATION: hsa-miR-571

<400> SEQUENCE: 17
tgagttggcc atctgagtga g                                              21

<210> SEQ ID NO 18
<211> LENGTH: 22
<212> TYPE: DNA
<213> ORGANISM: Artificial Sequence
<220> FEATURE:
<223> OTHER INFORMATION: hsa-miR-592

<400> SEQUENCE: 18
ttgtgtcaat atgcgatgat gt                                             22

<210> SEQ ID NO 19
<211> LENGTH: 21
<212> TYPE: DNA
<213> ORGANISM: Artificial Sequence
<220> FEATURE:
<223> OTHER INFORMATION: hsa-miR-629

<400> SEQUENCE: 19
tgggtttacg ttgggagaac t                                              21

<210> SEQ ID NO 20
<211> LENGTH: 22
<212> TYPE: DNA
<213> ORGANISM: Artificial Sequence
<220> FEATURE:
<223> OTHER INFORMATION: hsa-miR-654-3p
```

```
<400> SEQUENCE: 20
tatgtctgct gaccatcacc tt                                              22

<210> SEQ ID NO 21
<211> LENGTH: 22
<212> TYPE: DNA
<213> ORGANISM: Artificial Sequence
<220> FEATURE:
<223> OTHER INFORMATION: hsa-miR-1271

<400> SEQUENCE: 21
cttggcacct agcaagcact ca                                              22

<210> SEQ ID NO 22
<211> LENGTH: 24
<212> TYPE: DNA
<213> ORGANISM: Artificial Sequence
<220> FEATURE:
<223> OTHER INFORMATION: hsa-miR-20a

<400> SEQUENCE: 22
taaagttgct tatagtgcag gtag                                            24

<210> SEQ ID NO 23
<211> LENGTH: 23
<212> TYPE: DNA
<213> ORGANISM: Artificial Sequence
<220> FEATURE:
<223> OTHER INFORMATION: hsa-miR-142-3p

<400> SEQUENCE: 23
tgtagtgttt cctactttat gga                                             23

<210> SEQ ID NO 24
<211> LENGTH: 22
<212> TYPE: DNA
<213> ORGANISM: Artificial Sequence
<220> FEATURE:
<223> OTHER INFORMATION: hsa-miR-196

<400> SEQUENCE: 24
taggtagttt catgttgttg gg                                              22

<210> SEQ ID NO 25
<211> LENGTH: 22
<212> TYPE: DNA
<213> ORGANISM: Artificial Sequence
<220> FEATURE:
<223> OTHER INFORMATION: hsa-miR-223

<400> SEQUENCE: 25
tgtcagtttg tcaaataccc ca                                              22

<210> SEQ ID NO 26
<211> LENGTH: 22
<212> TYPE: DNA
<213> ORGANISM: Artificial Sequence
<220> FEATURE:
<223> OTHER INFORMATION: hsa-miR-450a

<400> SEQUENCE: 26
ttttgcgatg tgttcctaat at                                              22

<210> SEQ ID NO 27
```

```
<211> LENGTH: 22
<212> TYPE: DNA
<213> ORGANISM: Artificial Sequence
<220> FEATURE:
<223> OTHER INFORMATION: hsa-miR-451

<400> SEQUENCE: 27
aaaccgttac cattactgag tt                                              22

<210> SEQ ID NO 28
<211> LENGTH: 22
<212> TYPE: DNA
<213> ORGANISM: Artificial Sequence
<220> FEATURE:
<223> OTHER INFORMATION: hsa-miR-542-3p

<400> SEQUENCE: 28
tgtgacagat tgataactga aa                                              22

<210> SEQ ID NO 29
<211> LENGTH: 23
<212> TYPE: DNA
<213> ORGANISM: Artificial Sequence
<220> FEATURE:
<223> OTHER INFORMATION: hsa-miR-582-5p

<400> SEQUENCE: 29
ttacagttgt tcaaccagtt act                                             23

<210> SEQ ID NO 30
<211> LENGTH: 22
<212> TYPE: DNA
<213> ORGANISM: Artificial Sequence
<220> FEATURE:
<223> OTHER INFORMATION: P_hsa-miR-20a

<400> SEQUENCE: 30
actgcattat gagcacttaa ag                                              22

<210> SEQ ID NO 31
<211> LENGTH: 23
<212> TYPE: DNA
<213> ORGANISM: Artificial Sequence
<220> FEATURE:
<223> OTHER INFORMATION: P_hsa-miR-142-3p

<400> SEQUENCE: 31
tgtagtgttt cctactttat gga                                             23

<210> SEQ ID NO 32
<211> LENGTH: 21
<212> TYPE: DNA
<213> ORGANISM: Artificial Sequence
<220> FEATURE:
<223> OTHER INFORMATION: P_hsa-miR-196

<400> SEQUENCE: 32
taggtagttt catgttgttg g                                               21

<210> SEQ ID NO 33
<211> LENGTH: 22
<212> TYPE: DNA
<213> ORGANISM: Artificial Sequence
<220> FEATURE:
<223> OTHER INFORMATION: P_hsa-miR-223

<400> SEQUENCE: 33
```

```
tgtcagtttg tcaaataccc ca                                              22

<210> SEQ ID NO 34
<211> LENGTH: 22
<212> TYPE: DNA
<213> ORGANISM: Artificial Sequence
<220> FEATURE:
<223> OTHER INFORMATION: P_hsa-miR-450a

<400> SEQUENCE: 34
ttttgcgatg tgttcctaat at                                              22

<210> SEQ ID NO 35
<211> LENGTH: 22
<212> TYPE: DNA
<213> ORGANISM: Artificial Sequence
<220> FEATURE:
<223> OTHER INFORMATION: P_hsa-miR-451

<400> SEQUENCE: 35
aaaccgttac cattactgag tt                                              22

<210> SEQ ID NO 36
<211> LENGTH: 22
<212> TYPE: DNA
<213> ORGANISM: Artificial Sequence
<220> FEATURE:
<223> OTHER INFORMATION: P_hsa-miR-542-3p

<400> SEQUENCE: 36
tgtgacagat tgataactga aa                                              22

<210> SEQ ID NO 37
<211> LENGTH: 23
<212> TYPE: DNA
<213> ORGANISM: Artificial Sequence
<220> FEATURE:
<223> OTHER INFORMATION: P_hsa-miR-582-5p

<400> SEQUENCE: 37
ttacagttgt tcaaccagtt act                                             23
```

COMPOSITION FOR DIAGNOSING RECURRING GLIOBLASTOMA MULTIFORME AND METHOD FOR DIAGNOSING SAME

CROSS-REFERENCE TO RELATED APPLICATIONS

This application is a continuation of International Application No. PCT/KR2013/006519 filed on Jul. 22, 2013, which claims priority to Korean Application No. 10-2012-0079314 filed on Jul. 20, 2012. The applications are incorporated herein by reference.

TECHNICAL FIELD

This application claims a priority from and the benefit of Korean Patent Application No. 10-2012-0079314, filed on Jul. 20, 2012, all of which are incorporated herein by reference in its entirety for all purposes as if fully set forth herein.

The present invention relates to a recurring glioblastoma multiforme marker miRNA for diagnosing recurring glioblastoma multiforme, and more specifically, to a composition for screening the miRNA marker, which is specific to the recurring glioblastoma multiforme and comprises an agent for detecting the presence of the marker, a kit, and to a method for diagnosing the recurring glioblastoma multiforme using same.

BACKGROUND ART

MicroRNAs (miRNAs) are single-stranded endogenous non-coding small RNA molecules of about 18-25 nucleotides in length, which negatively regulate gene expression either by binding to the 3' UTR leading to inhibition of translation or degradation of specific target mRNAs. A single miRNA can directly regulate multiple target genes, and thereby control expressions of multiple proteins involved in diverse signaling pathways (Bartel D P. MicroRNAs: target recognition and regulatory functions. Cell 2009; 136:215-233). The expressions of miRNAs differ according to organ development and tissue differentiation (Rosenfeld N, Aharonov R, Meiri E, et al. MicroRNAs accurately identify cancer tissue origin. Nat Biotechnol 2008; 26:462-469). MiRNAs are known to regulate diverse biological processes (Huang Y, Shen X J, Zou Q, Wang S P, Tang S M Zhang G Z. Biological functions of microRNAs: a review. Journal of physiology and biochemistry 2011; 67:129-139), and are associated with apoptosis and cancer by regulating the translation of oncogenes and tumor suppressors (Lee Y S Dutta A. MicroRNAs in cancer. Annu Rev Pathol 2009; 4:199-227). Recent studies have demonstrated dysregulation of miRNAs in the initiation and progression of various cancers (Lovat F, Valeri N Croce C M. MicroRNAs in the pathogenesis of cancer. Seminars in oncology 2011; 38:724-733).

Glioblastoma multiforme (GBM, World Health Organization [WHO] grade IV glioma) is the most common and aggressive type of primary adult brain cancer. The standard treatment for newly diagnosed GBM is surgical resection followed by a combination of radiation and chemotherapy (Stupp R, Mason W P, van den Bent M J, et al. Radiotherapy plus concomitant and adjuvant temozolomide for glioblastoma. N Engl J Med 2005; 352:987-996). Despite advances in therapeutic approaches and the understanding of the molecular mechanisms and genetics of GBM (Bai R Y, Staedtke V Riggins G J. Molecular targeting of glioblastoma: Drug discovery and therapies. Trends in molecular medicine 2011; 17:301-312, Kesari S. Understanding glioblastoma tumor biology: the potential to improve current diagnosis and treatments. Seminars in oncology 2011; 38 Suppl 4:S2-10), the overall survival rate is very poor and the median lifespan of GBM patients is limited to 10 to 15 months. This lifespan has only minimally improved over a period of decade even with therapeutic interventions. The major problem is that most GBM (about 90% of cases) recurs within or adjacent to the original tumor bed (Joki T, Carroll R S, Dunn I F, Zhang J, Abe T Black P M. Assessment of alterations in gene expression in recurrent malignant glioma after radiotherapy using complementary deoxyribonucleic acid microarrays. Neurosurgery 2001; 48:195-201; discussion 201-192). Currently, there is no standard treatment for recurrent GBM, although additional surgery, chemotherapy, and radiotherapy are used. Therefore, it is urgently necessary to determine novel molecular targets, concepts, and approaches to treat this devastating disease.

Since human brain tumor stem cells have been identified, researches on the resistance of GBM to chemoradiotherapy have been conducted. The resistance is attributed to a DNA repair proficiency, a multitude of dysregulated growth factor signaling pathways, and to the particular biologic behaviors of cancer stem-like cells (Haar C P, Hebbar P, Wallace G Ct, et al. Drug Resistance in Glioblastoma: A Mini Review. Neurochemical research 2012). Although the molecular and genetic changes in recurrent GBM have been studied, the causes and pathogenesis of resistance in recurrent GBM have not yet been clearly identified.

As postoperative radiotherapy does not provide great benefits to GBM patients, several attempts have been made to find suitable adjuvant chemotherapies to prevent the recurrence of GBM. A novel approach for the molecular characterization of tumors is based on the expression profiling of miRNAs. Over the past few years, several miRNAs involved in GBM pathogenesis have been identified (Novakova J, Slaby O, Vyzula R Michalek J. MicroRNA involvement in glioblastoma pathogenesis. Biochem Biophys Res Commun 2009; 386:1-5, Srinivasan S, Patric I R Somasundaram K. A ten-microRNA expression signature predicts survival in glioblastoma. PLoS One 2011; 6:e17438); however, the physiological roles of only small fraction of the identified miRNA are understood. Moreover, global miRNA signature involved in the resistance of recurrent GBM has never been investigated.

SUMMARY

The present inventors, while searching for effective methods for treating and preventing recurring glioblastoma multiforme, have endeavored to found markers specific to recurring glioblastoma multiforme, the markers diagnosing recurring glioblastoma multiforme through miRNAs expressed in recurring glioblastoma multiforme cells, and then have completed the present invention.

Therefore, the present invention has been made in view of the above-mentioned problems, and an aspect of the present invention is to provide a composition for diagnosing recurring glioblastoma multiforme, the composition comprising the miRNA represented by SEQ ID NO: 1.

Another aspect of the present invention is to provide a use of the miRNA represented by SEQ ID NO: 1, for preparing an agent for diagnosing recurring glioblastoma multiforme.

Still another aspect of the present invention is to provide a method for diagnosing recurring glioblastoma multiforme, the method comprising:

(a) measuring the expression level of the miRNA represented by SEQ ID NO: 1 obtained from a biological sample isolated from a suspected patient with recurring glioblastoma multiforme;

(b) comparing the expression level of the miRNA with the expression level of a corresponding miRNA of a normal control sample.

Still another aspect of the present invention is to provide a kit for diagnosing recurring glioblastoma multiforme, the kit including an agent for measuring the expression level of the miRNA represented by SEQ ID NO: 1.

In accordance with an aspect of the present invention, there is provided a composition for diagnosing recurring glioblastoma multiforme, the composition comprising the miRNA represented by SEQ ID NO: 1.

In accordance with another aspect of the present invention, there is provided a use of the miRNA represented by SEQ ID NO: 1 for preparing an agent for diagnosing recurring glioblastoma multiforme.

In accordance with still another aspect of the present invention, there is provided a method for diagnosing recurring glioblastoma multiforme, the method comprising:

(a) measuring the expression level of the miRNA represented by SEQ ID NO: 1 obtained from a biological sample isolated from a suspected patient with recurring glioblastoma multiforme;

(b) comparing the expression level of the miRNA with the expression level of a corresponding miRNA of a normal control sample.

In accordance with still another aspect of the present invention, there is provided a kit for diagnosing recurring glioblastoma multiforme, the kit including an agent for measuring the expression level of the miRNA represented by SEQ ID NO: 1.

As set forth above, the present invention provides a composition for diagnosing recurring glioblastoma multiforme and a method for diagnosis using the same. The composition for diagnosing recurring glioblastoma multiforme and the method for diagnosis using the same provide markers capable of diagnosing the occurrence of recurring glioblastoma multiforme, thereby providing data useful for the treatment and prognosis management of recurring glioblastoma multiforme. Furthermore, the markers for diagnosing recurring glioblastoma multiforme can be used in research and development of anti-cancer drugs specific to recurring glioblastoma multiforme.

DETAILED DESCRIPTION

Figure 1:
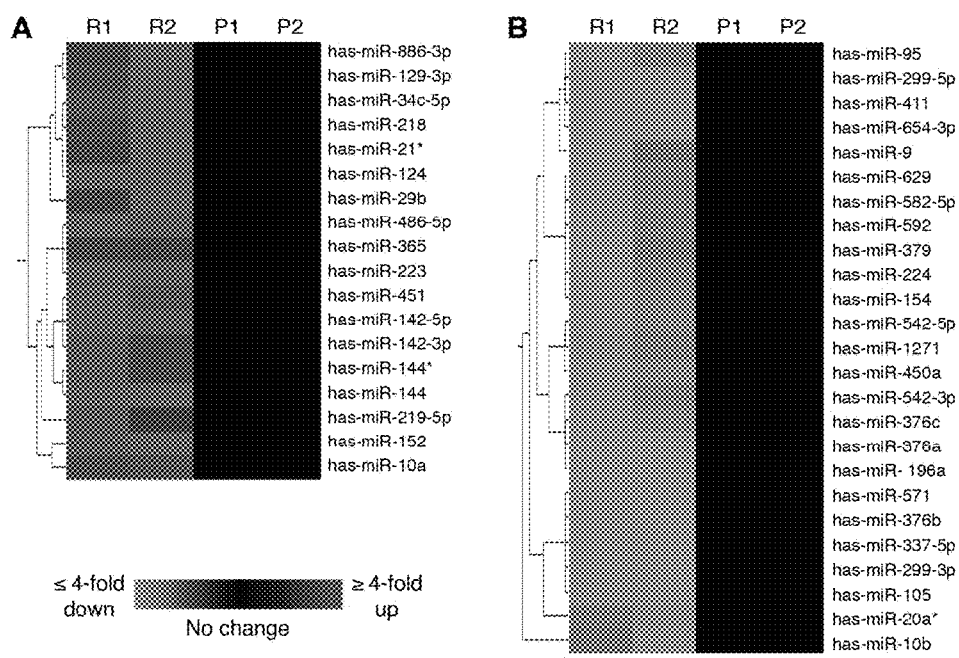
FIG. 1 shows heat map analysis of the differentially expressed miRNAs in recurrent GBM. Each row represents the relative levels of expression for a single miRNA and each column shows the expression levels for a single sample. The red or green color indicates relative high or low expression, respectively, as standard bar. R1, recurrent GBM patient 1; R2, recurrent GBM patient 2; P1, primary GBM patient 1; P2, primary GBM patient 2.

The present invention provides a composition for diagnosing recurring glioblastoma multiforme, comprising the miRNA represented by SEQ ID NO: 1. The composition may contain at least one miRNA selected from the group consisting of SEQ ID NOS: 1 to 29. Further, the present invention provides a use of the miRNA represented by SEQ ID NO: 1 for preparing an agent for diagnosing recurring glioblastoma multiforme.

The term recurring glioblastoma multiforme indicates the recurrence of glioblastoma multiforme, which is a tumor generated in brain nerve cells, and refers to glioblastoma multiforme recurring in a part where glioblastoma multiforme had occurred before or glioblastoma multiforme recurring around the part.

SEQ ID NO: 1 (hsa-miR-365, taatgccccctaaaaatccttat) is one of miRNAs differently expressed in recurring GBM confirmed in an example, and it was confirmed that the miRNA of SEQ ID NO: 1 showed more change in recurring GBM when compared with normal GBM and incipient GBM.

Meanwhile, the composition or agent of the present invention may contain at least one miRNA selected from the group consisting of SEQ ID NOS: 2 to 29 in addition to the miRNA of SEQ ID NO: 1. Respective usual names for the sequences are as follows: SEQ ID NO: 2 (hsa-miR-29b, tagcaccatttgaaatcagtgtt), SEQ ID NO: 3 (hsa-miR-34c-5p, aggcagtgtagttagctgattgc), SEQ ID NO: 4 (hsa-miR-129-3p, aagcccttaccccaaaaagcat), SEQ ID NO: 5 (hsa-miR-218, ttgtgcttgatctaaccatgt), SEQ ID NO: 6 (hsa-miR-124, taaggcacgcggtgaatgcc), SEQ ID NO: 7 (hsa-miR-486-5p, tcctgtactgagctgccccgag), SEQ ID NO: 8 (hsa-miR-10b, taccctgtagaaccgaatttgtg), SEQ ID NO: 9 (hsa-miR-95, ttcaacgggtatttattgagca), SEQ ID NO: 10 (hsa-miR-154, taggttatccgtgttgccttcg), SEQ ID NO: 11 (hsa-miR-224, caagtcactagtggttccgtt), SEQ ID NO: 12 (hsa-miR-299-3p, tatgtgggatggtaaaccgctt), SEQ ID NO: 13 (hsa-miR-299-5p, tggtttaccgtcccacatacat), SEQ ID NO: 14 (hsa-miR-376a, atcatagaggaaaatccacgt), SEQ ID NO: 15 (hsa-miR-376c, aacatagaggaaattccacgt), SEQ ID NO: 16 (hsa-miR-379, tggtagactatggaacgtagg), SEQ ID NO: 17 (hsa-miR-571, tgagttggccatctgagtgag), SEQ ID NO: 18 (hsa-miR-592, ttgtgtcaatatgcgatgatgt), SEQ ID NO: 19 (hsa-miR-629, tgggtttacgttgggagaact), SEQ ID NO: 20 (hsa-miR-654-3p, tatgtctgctgaccatcacctt), SEQ ID NO: 21 (hsa-miR-1271, cttggcacctagcaagcactca), SEQ ID NO: 22 (hsa-miR-20a, taaagttgcttatagtgcaggtag), SEQ ID NO: 23 (hsa-miR-142-3p, tgtagtgtttcctactttatgga), SEQ ID NO: 24 (hsa-miR-196, tagggagtttcatgttgttggg), SEQ ID NO: 25 (hsa-miR-223, tgtcagtttgtcaaataccca), SEQ ID NO: 26 (hsa-miR-450a, ttttgcgatgtgttcctaatat), SEQ ID NO: 27 (hsa-miR-451, aaaccgttaccattactgagtt), SEQ ID NO: 28 (hsa-miR-542-3p, tgtgacagattgataactgaaa), SEQ ID NO: 29 (hsa-miR-582-5p, ttacagttgttcaaccagttact).

A preferable use of the miRNA represented by SEQ ID NO: 1 is a preparation of an agent for diagnosing recurring glioblastoma multiforme. Descriptions of the agent for diagnosis are the same as those of the composition for diagnosis.

The miRNA is a specific marker which is expressed more than two times in the recurring glioblastoma multiforme than a normal control group, and the expression level thereof enables the diagnosis of recurring glioblastoma multiforme. In addition, the miRNAs of SEQ ID NOS: 2 to 29 can be used to prepare the agent for diagnosing recurring glioblastoma multiforme. The miRNAs of SEQ ID NOS: 2 to 7, SEQ ID NO: 23, SEQ ID NO: 25, and SEQ ID NO: 27 are expressed more than two times in patients with recurring glioblastoma multiforme than a normal control group, and the miRNAs of SEQ ID NOS: 8 to 22, SEQ ID NO: 24, SEQ ID NO: 26, SEQ ID NO: 28, and SEQ ID NO: 29 are expressed less than a half in the patients with recurring glioblastoma multiforme than the normal control group.

The miRNAs of SEQ ID NOS: 1 to 29 may be markers for diagnosing recurring glioblastoma multiforme. Therefore, the present invention provides a kit including an agent capable of detecting the marker for diagnosing recurring glioblastoma multiforme, that is, a kit for diagnosing recurring glioblastoma multiforme, the kit including an agent for measuring the expression level of the miRNA represented by SEQ ID NO: 1. In addition, the kit for diagnosis of the present invention may further include an agent for measuring the expression level of the miRNA selected from the group consisting of SEQ ID NOS: 2 to 29.

Preferably, the agent can confirm the expression levels of miRNAs, which are markers for diagnosing recurring glioblastoma multiforme, obtained from biological samples, and can measure the amounts of miRNAs. The analysis methods therefor are reverse transcription-polymerase chain reaction (RT-PCR), competitive RT-PCR, real-time RT-PCR, RNase protection assay (RPA), northern blotting, DNA chip assay, and the like, but are not limited thereto.

Preferably, the agent may be a PCR primer for amplifying a corresponding miRNA. Preferable examples of the primer may be SEQ ID NO: 30 (primer for hsa-miR-20a; ACTG-CATTATGAGCACTTAAAG), SEQ ID NO: 31 (primer for hsa-miR-142-3p; TGTAGTGTTTCCTACTTTATGGA), SEQ ID NO: 32 (primer for hsa-miR-196; TAGG-TAGTTTCATGTTGTTGG), SEQ ID NO: 33 (primer for hsa-miR-223; TGTCAGTTTGTCAAATACCCCA), SEQ ID NO: 34 (primer for hsa-miR-450a; TTTTGCGATGTGT-TCCTAATAT), SEQ ID NO: 35 (primer for hsa-miR-451; AAACCGTTACCATTACTGAGTT), SEQ ID NO: 36 (primer for hsa-miR-542-3p; TGTGACAGATTGATAACT-GAAA), SEQ ID NO: 37 (primer for hsa-miR-582-5p; TTACAGTTGTTCAACCAGTTACT). (As for the PCR primer for each miRNA, PCR is possible only one PCR primer since each miRNA itself can serve as a primer). The primer is a nucleotide having a sequence specific to each miRNA, and has a length of about 16 bp to 30 bp, and more preferably about 21 bp to 23 bp. In addition, the primer may be a primer selected from SEQ IDS NO: 22 to 29.

In addition, the kit for diagnosing recurring glioblastoma multiforme of the present invention may include one or more kinds of constituent compositions, solutions, or devices, which are suitable for the analysis method.

The kit for diagnosis may be a kit for diagnosis, characterized by including necessary components required to perform real-time RT-PCR. The real-time RT-PCR kit includes primers specific to marker miRNAs. The kit of the present invention may include at least one of primers of SEQ ID NOS: 30 to 37. In addition, other real-time RT-PCR kits may include a test tube or appropriate container, a buffer (various pH values and magnesium concentrations), deoxynucleotide (dNTPs), enzymes such as Taq-polymerase and reverse transcriptase, DNAse and RNAse inhibitors, DEPC-water, sterilized water, and the like.

The present invention provides a method for diagnosing recurring glioblastoma multiforme, the method comprising: (a) measuring the expression level of the miRNA of SEQ ID NO: 1 obtained from a biological sample isolated from a suspected patient with recurring glioblastoma multiforme; and (b) comparing the expression level of the miRNA with the expression level of a corresponding miRNA of a normal control sample.

(a) Step of measuring expression level of miRNA represented by SEQ ID NO: 1 obtained from biological sample isolated from suspected patient of recurring glioblastoma multiforme:

The isolation of the miRNA from a biological sample may be performed using a known process, and the expression level of the miRNA may be measured by various methods.

The biological sample includes tissues, cells, whole blood, serum, plasma, saliva, sputum, cerebrospinal fluid, and urine, which have different expression levels of miRNA, as a marker for recurring glioblastoma multiforme, due to the occurrence of recurring glioblastoma multiforme, but is not limited thereto.

The analysis methods for measuring the expression level of the miRNA are RT-PCR, competitive RT-PCR, real-time RT-PCR, RNase protection assay, northern blotting, DNA chip assay, and the like, but are not limited thereto.

The assay methods can compare the expression level of the miRNA in a normal control group with the expression level of the miRNA in a suspected patient with recurring glioblastoma multiforme, and determine the significant increase or not of the expression level of the miRNA as a marker for recurring glioblastoma multiforme, thereby diagnosing the actual occurrence or not of recurring glioblastoma multiforme of the suspected patient with recurring glioblastoma multiforme.

The expression level of the miRNA is measured by, preferably, by a real-time PCR method or DNA chip assay, which uses a primer specific to a gene used as a marker for recurring glioblastoma multiforme.

After the real-time RT-PCR, electrophoresis is performed to check the patterns and thicknesses of bands, thereby confirming the presence or absence of the expression and the expression level of the miRNA used as a marker for diagnosing recurring glioblastoma multiforme, and the expression level of the miRNA is compared with the expression level of the miRNA of a control group, thereby conveniently diagnosing whether or not recurring glioblastoma multiforme occurs.

(b) Step of comparing expression level of miRNA with expression level of corresponding miRNA of normal control sample:

When comparing the expression level of miRNA of SEQ ID NO: 1 between a suspected patient with recurring glioblastoma multiforme and a normal control group, if the miRNA is expressed more than two times in the suspected patient, the suspected patient may be diagnosed with recurring glioblastoma multiforme. The normal control group is a generic term for persons except patients with recurring glioblastoma multiforme.

The method for diagnosing recurring glioblastoma multiforme of the present invention is performed using the expression level of the miRNA of SEQ ID NOS: 2 to 29 besides the miRNA of SEQ ID NO: 1. If the miRNA selected from the group consisting of SEQ ID NOS: 2 to 7, SEQ ID NO: 23, SEQ ID NO: 25, and SEQ ID NO: 27 is expressed more than two times in a patient with recurring glioblastoma multiforme than a normal control group, and the miRNA selected from the group consisting of SEQ ID NOS: 8 to 22, SEQ ID NO: 24, SEQ ID NO: 26, SEQ ID NO: 28, and SEQ ID NO: 29 is expressed less than a half in the patient with recurring glioblastoma multiforme than the normal control group, the patient may be diagnosed with recurring glioblastoma multiforme.

EXAMPLES

Hereinafter, the present invention will be described in detail by examples. It is to be understood, however, that these examples are for illustrative purpose only and are not construed to limit the scope of the present invention.

<Experimental Method>

1. Patient Samples

This study was approved by the institutional review board of the Catholic University of Korea (KC10SISI042). Human GBM samples were obtained from two primary GBM patients during definitive surgery and two recurrent GBM patients during salvage surgery. The recurrent GBM samples were from patients who had been treated with total tumor removal followed by concomitant temozolomide based chemoraidotherapy. Radiotherapy was given up to a total 59.5 Gy on the surgical bed with margin by conformal technique. The characteristics of the patients were shown in Table 1.

TABLE 1

Patient characteristics.

| Patient no. | Diagnosis | Sex/Age | WHO grade | Ki-67 | p53 | MGMT [a] | MGMT methylaiton | Radiotherapy |
|---|---|---|---|---|---|---|---|---|
| P1 | GBM | F/68 | IV | 20% | positive | 40-50% positive | n/a [b] | no |
| P2 | GBM | F/78 | IV | 30% | positive | 35% positive | n/a | no |
| R1 | Recurrent GBM | M/45 | IV | 80% | positive | 60-70% positive | positive | CCRT [c] 59.4Gy |
| R2 | Recurrent GBM | M/38 | IV | 40% | positive | >40% positive | n/a | CCRT 59.4 Gy |

[a] MGMT, O$^6$-methylguanine-DNA methyltransferase.
[b] Not available.
[c] CCRT, Concurrent chemoradiotherapy, temozolomide based.

2. RNA Isolation

Total RNA extraction and miRNA microarray analysis were performed as described (Kim G, Park E C, Ryu C H, et al. MicroRNA expression profiling in recurrent anaplastic oligodendroglioma treate with postoperative radiotherapy. J Anal Sci & Technol 2011; 2:97-104). Samples were homogenized with TRI Reagent (Molecular Research Center, Cincinnati, Ohio) and the supernatant was vigorously mixed with BCP (1-bromo-3-chloropropane, Molecular Research Center) for phase separation. After centrifugation at 12,000 rpm for 10 min. at 4° C., the aqueous phase was used for further phenolchloroform extraction, and the total RNA was precipitated and dissolved in RNase-free water. The RNA was qualified by using an Agilent 2100 Bioanalyzer (Agilent Technologies, Santa Clara, Calif.).

3. MiRNA Microarray Analysis

The synthesis of target miRNA probes and hybridization were performed using an Agilent's miRNA Labeling Reagent and Hybridization kit. Briefly, each 100 ng of total RNA was dephosphorylated with 15 units of calf intestine alkaline phosphatase, followed by RNA denaturation with 40% DMSO for 10 min. at 100° C. The dephosphorylated RNA was ligated with pCp-Cy3 mononucleotides and purified with MicroBioSpin 6 columns (Bio-Rad, Hercules, Calif., USA). After purification, labeled samples were resuspended with a Gene Expression Blocking Reagent and an Hi-RPM Hybridization Buffer, followed by boiling for 5 min. at 100° C. and 5 min. chilling on ice. Finally, the denatured labeled probes were pipetted onto assembled Agilent miRNA Microarray (15K) and hybridized for 20 hours at 55° C. at 20 rpm rotating in an Agilent Hybridization Oven. The hybridized microarrays were washed according to the manufacturer's washing protocol and scanned on an Agilent G2404B Scanner. The scanned images were extracted with Feature Extraction software (Agilent Technologies) using default parameters for background correction.

4. MiRNA First-Strand cDNA Synthesis and Quantitative Real Time PCR

To synthesis miRNA first-strand cDNA from the total RNA, polyadenylation and reverse transcription of miRNA were performed using a Mir-X™ miRNA first-strand synthesis Kit (Takara Bio, Shiga, Japan) according to the manufacturer's instructions. For the quantification of the target miRNAs, real time PCR was conducted with a SmartCycler® System (Cepheid) using SYBR® Premix Ex Taq™ II (Takara Bio). The forward primer of each of target miRNA is SEQ ID NOS:22 to 29, and the reverse primer of each of target miRNA is SEQ ID NOS:30 to 37. Since miRNA itself could act as a PCR primer for amplifying the miRNA, miRNA cDNA could be prepared by PCR reaction using only forward primer or reverse primer.

5. Bioinformatic Analysis of miRNA Targets and Associated Pathways

Targets for up- and down-regulated miRNAs were searched from public resources, miRanda (http://www.microrna.org/microrna/home.do) and miRbase (http://mirbase.org/) databases. For the pathway analysis, we collected major pathways from KEGG (http://www.genome.jp/kegg/) and NCI-Nature curated (http://pid.nci.nih.gov/browse_pathways.shtml). Each pathway database was cumulated into one single file, and then, using the target genes from up- or down-regulated miRNAs the number of matched genes in each pathway was counted with the total genes in the given pathway, sorted by the number of matched genes and the top 10 pathways were selected.

<Result>

1. Identification of Differentially Expressed miRNAs in Recurrent GBM

To identify the miRNAs involved in the resistance of recurrent GBM, we performed a comprehensive analysis of the miRNA transcription profiles between the newly-diagnosed GBM and the recurrent GBM treated with postoperative chemoradiotherapy. Human brain tissues were obtained from two patients in the primary GBM group and from two patients in the recurrent GBM group. A total of 318 miRNAs were expressed in the GBM patients. Out of the 318 identified miRNAs, 43 showed at least 2-fold changes in expression levels in both the recurrent GBM patients. Eighteen miRNAs were upregulated and 25 miRNAs were down-regulated in the recurrent GBM patients (FIG. 1).

2. Validation of the Selected miRNAs Expression by Quantitative RT-PCR

Figure 2:
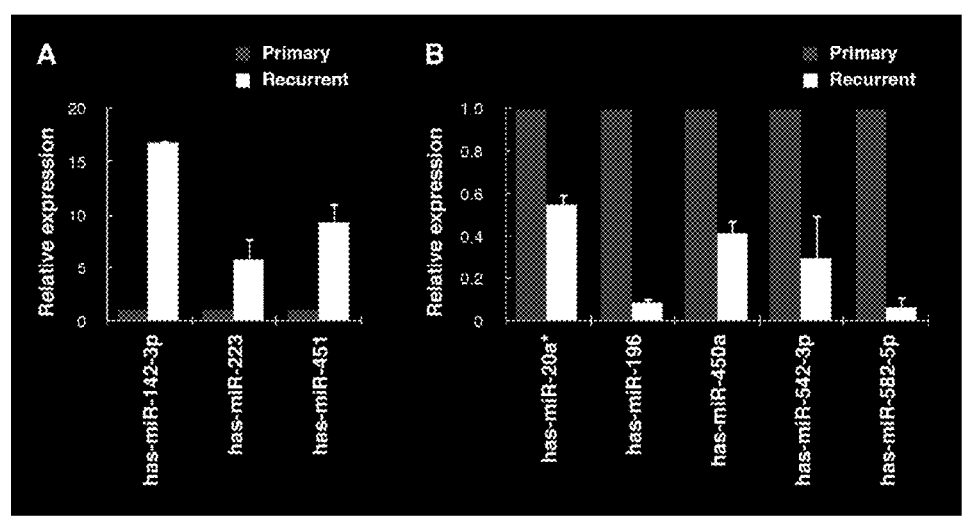
FIG. 2 shows real-time RT-PCR validation of microarray of 3 up-regulated miRNAs (A) and 5 down-regulated miRNAs (B). The expression level of indicated miRNA was compared between primary and recurrent GBMs. RNU6-1 RNA was used as a internal control for miRNA expression.
Figure 3:
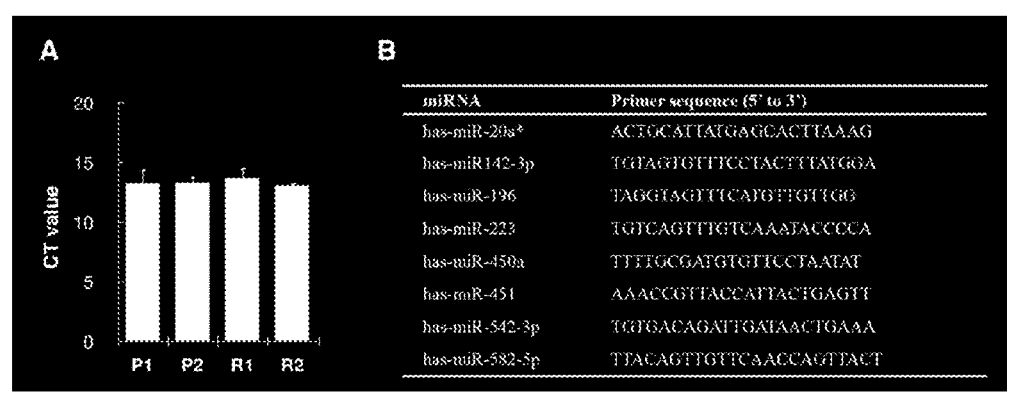
FIG. 3 shows the expression level of RNU6-1 RNA which is related to primary and recurrent GBMs, by real-time RT-PCR. P: primary GBM patient, R1: recurrent GBM patient 1, R2: recurrent GBM patient 2. The primer sequences shown in the figure correspond to SEQ ID Nos: 30-37 (from top to bottom).

To confirm the results of the miRNA array analysis, quantitative RT-PCR (qRT-PCR) was carried out. Prior to performing RT-PCR it was necessary to determine an endogenous control gene for normalization of miRNA transcript expression. RNU6-1 expression was comparable between the recurrent GBM patients and unaffected by the recurrence of GBM (FIG. 3). To validate expression changes of miRNAs detected in the microarray, qRT-PCR was performed on 8 miRNAs (randomly selected): has-miR-20a*, has-miR-142-3p, has-miR-196, has-miR-223, has-miR-450a, has-miR-451, has-miR-542-3p, and has-miR-582-5p. In agreement with the miRNA microarray result, has-miR-142-3p, has-miR-223, and has-miR-451 were upregulated (FIG. 2A) and has-miR-20a*, has-miR-196, has-miR-450a, has-miR-542-3p, and has-miR-582-5p were down-regulated (FIG. 2B) in the recurrent GBM patients.

3. Knowledge-Based Bioinformatic Analysis of miRNAs

To identify molecular and cellular networks related to the differentially expressed miRNAs in recurrent GBM after chemoradiotherapy, we performed knowledge-based Ingenuity Pathway Analysis (IPA) using the 43 miRNAs that experienced greater than 2-fold changes in expression levels. IPA identified the cell death as the top category followed by the cellular development and the cellular growth and proliferation as significantly associated with the miRNAs. Core analysis using IPA generated a network containing the 12 identified miRNAs and key proteins associated with cancer and cell death (FIG. 5). The network identified tumor suppressor gene TP53 as a central node although none of the miRNAs directly regulate p53 expression. Therefore, it suggests that the alteration of p53 signaling and expression of its effectors may be responsible for the recurrence of the GBM.

4. Bioinformatic Analysis of miRNAs Target Genes and Associated Cellular Pathways We conducted a bioinformatic analysis of the miRNAs to identify those with potential target genes may be involved in resistance to chemoradiotherapy and recurrence processes of GBM. The potential target genes of the 43 differentially expressed miRNAs were identified in silico, and then pathway enrichment analysis was performed with Kyoto Encyclopedia of Genes and Genomes (KEGG) database to explore the possible biological impact of the miRNAs in recurrent GBM. As expected, target genes of the miRNAs were enriched in pathways associated with cancer (Table 2).

TABLE 2

Analysis of pathways associated with target genes of miRNAs in recurrent GBM.

| Pathway [a] | No. of miRNA target genes [b] | % [c] |
|---|---|---|
| KEGG | | |
| Metabolic pathways | 447 genes among 1116 genes | 38.3 |
| Pathways in cancer | 231 genes among 328 genes | 70.4 |
| MAPK signaling pathway | 171 genes among 271 genes | 63.1 |
| Cytokine-cytokine receptor interaction | 146 genes among 275 genes | 53.1 |
| Regulation of actin cytoskeleton | 141 genes among 216 genes | 65.3 |
| Neuroactive ligand-receptor interaction | 140 genes among 318 genes | 44 |
| Focal adhesion | 135 genes among 201 genes | 67.2 |
| Endocytosis | 129 genes among 205 genes | 62.9 |
| Wnt signaling pathway | 111 genes among 151 genes | 73.5 |
| Calcium signaling pathway | 104 genes among 178 genes | 37.4 |
| NCI-Nature curated | | |
| Direct p53 effectors | 90 genes among 138 genes | 65.2 |
| ErbB1 downstream signaling | 82 genes among 104 genes | 78.8 |
| Regulation of nuclear Smad2/3 signaling | 60 genes among 81 genes | 74.1 |
| c-Myb transcription factor network | 60 genes among 84 genes | 71.4 |
| Regulation of Wnt-mediated β-catenin signaling and target gene transcription | 58 genes among 80 genes | 72.5 |
| Validated targets of c-Myc transcriptional activation | 58 genes among 81 genes | 71.6 |
| Validated targets of c-Myc transcriptional repression | 51 genes among 63 genes | 81 |
| Signaling events mediated by HDAC class I | 51 genes among 66 genes | 77.3 |
| E2F transcription factor network | 49 genes among 71 genes | 69 |
| Notch signaling pathway | 46 genes among 58 genes | 79.3 |

[a] Target genes were analyzed by using Kyoto Encyclopedia of Genes and Genomes (KEGG) and National Cancer Institute (NCI)-Nature curated database.
[b] Number of miRNA target genes among number of genes that are involved in each pathway. A full list of miRNAs and their target genes are not shown.
[c] Proportion of miRNA target genes from the total number of genes that belong to each pathway.

This includes proliferation, sustained angiogenesis, block of differentiation, evading apoptosis, tissue invasion and metastasis, failed repair of genes, genomic damage, and insensitivity to antigrowth signals. In addition, a number of genes involved in Wnt and mitogen-activated protein kinase (MAPK) signaling pathways were targeted by the miRNAs (Table 2). Wnt signaling acts to maintain the undifferentiated state of stem cells and MAPK mediates various growth factor signalings, such as epidermal growth factor (EGF), fibroblast growth factor (FGF), and platelet-derived growth factor (PDGF) that instruct the cells to proliferate (Nusse R. Wnt signaling and stem cell control. Cell research 2008; 18:523-527). It suggests that cancer tissues may become more aggressive and more proliferative in recurrent GBM after chemoradiotherapy.

Figure 4:
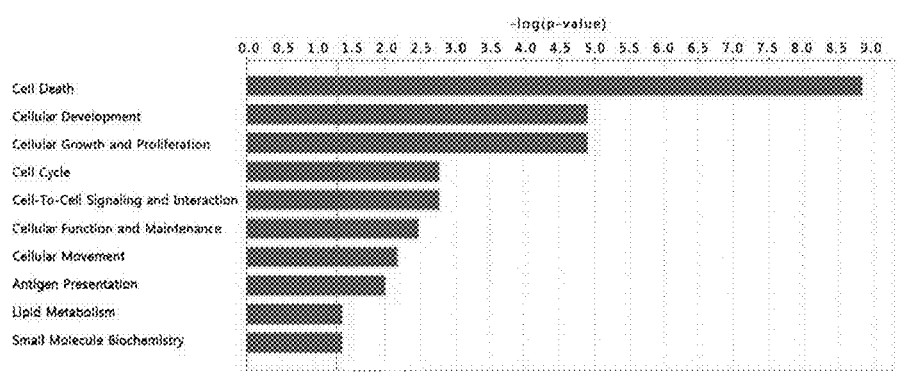
FIG. 4 shows result of Ingenuity Pathway Analysis (IPA), which shows relationships among 43 miRNAs differently expressed in recurrent GBMs.

To further investigate more detailed signaling pathways involved with the differentially expressed miRNAs in recurrent GBM, we extended pathway analysis using National Cancer Institute (NCI)-Nature curated database. It is found that the miRNA target genes were mainly associated with various growth factor signaling pathways, such as ErbB1 (also known as epidermal growth factor receptor, EGFR), Smad2/3, Wnt, and Notch (Table 2). We also noted that the miRNAs targeted the largest number of genes that regulated by p53 signaling (Table 2). This result highly coincided with that form the knowledge based IPA (FIG. 4).

Finally, to identify novel miRNAs that may be responsible for the recurrence of GBM, the putative genes from the miRNA target prediction were compared with the reference set of genes from the pathway analysis, and the overlaps between those sets of genes are listed. Seventy two direct p53 effector genes were identified by 18 up-regulated miR-NAs in recurrent GBM (Table 3).

TABLE 3

Predicted target of miRNAs exhibiting more than 2-fold expression increase in recurrent GBM.

| miRNA | Fold change [a] | Signaling pathway of target genes [b] Direct p53 effectors |
|---|---|---|
| hsa-miR-10a | 2.97 | BCL2L1, BCL2L14, BCL6, BNIP3L, DUSP5, E2F3, NFYA, PERP, PTEN |
| hsa-miR-21* | 3.6 | BNIP3L, DDB2, DUSP5, SH2D1A, TFDP1, TP53INP1, TP63 |
| hsa-miR-29b | 3.31 | BBC3, BCL2, BTG2, E2F1, E2F3, FAS, FOXA1, LIF, MET, MMP2, NFYB, PRDM1, PTEN, SESN1, SP1, TP53INP1 |
| hsa-miR-34c-5p | 7.67 | BCL2, CCNG1, CSE1L, DKK1, E2F3, HIC1, MAP4K4, MET, PCBP4, PIDD, PRMT1, PTEN, SCN3B, TGFA, TP53INP1, ZNF385A |
| hsa-miR-124 | 10.47 | BAK1, BCL6, BTG2, CAV1, E2F3, MAP4K4, SNAI2, SP1, TP53INP1, VCAN |
| hsa-miR-129-3p | 7.27 | BCL2L2, BNIP3L, DDB2, E2F3, MCL1, PERP, PLK3, RB1, RCHY1, RRM2B, TP63 |
| hsa-miR-142-3p | 2.97 | APC, ATF3, BNIP3L, E2F3, FOXA1, RCHY1, SP1, TP53INP1 |

TABLE 3-continued

Predicted target of miRNAs exhibiting more than 2-fold expression increase in recurrent GBM.

| miRNA | Fold change [a] | Signaling pathway of target genes [b] Direct p53 effectors |
|---|---|---|
| hsa-miR-142-5p | 4.22 | APAF1, ARID3A, CASP10, CCNK, CDKN1A, EP300, EPHA2, FOXA1, HGF, MAP4K4, MCL1, MET, PRDM1, PTEN, SH2D1A, TGFA, TP53INP1, TP63 |
| hsa-miR-144 | 6.34 | APAF1, BBC3, BCL2A1, BCL6, BNIP3L, BTG2, CAV1, CCNK, E2F3, FOXA1, PCNA, PTEN, RB1, SH2D1A, SP1, TP53INP1, TP63 |
| hsa-miR-144* [c] | 3.13 | |
| hsa-miR-152 | 4.46 | ARID3A, BBC3, CCNK, DKK1, E2F1, E2F3, EP300, FOXA1, GADD45A, MAP4K4, MET, NFYA, NFYB, PML, POU4F2, PTEN, RRM2B, TGFA |
| hsa-miR-218 | 5.32 | BTG2, CAV1, DUSP5, E2F2, FAS, LIF, SNAI2, SP1, STEAP3, TNFRSF10B |
| hsa-miR-219-5p | 2.74 | APAF1, BCL2, CREBBP |
| hsa-miR-223 | 3.67 | AIFM2, APC, BCL2, BNIP3L, C13orf15, CAV1, CCNG1, E2F1, MCL1, PRDM1, PTEN, RB1, SP1 |
| hsa-miR-365 | 2.46 | BAX, BCL2, BTG2, CCNG1, CDKN1A, HGF, POU4F2, PRDM1, SCN3B, TP63, TYRP1 |
| hsa-miR-451 | 3.56 | CAV1, VCAN |
| hsa-miR-486-5p | 3.89 | NFYA, PCBP4, PIDD, PPP1R13B, PTEN, TFDP1, TP53INP1 |
| hsa-miR-886-3p | 5.15 | BBC3, CAV1 |

[a] Average fold change (recurrent/primary).
[b] Abbreviations are shown in public database (Genbank or Swissprot).
[c] miRNA and miRNA* are derived from same miRNA precursor.

From 25 down-regulated miRNAs in recurrent GBM, 72 genes involved in ErbB1 downstream signaling, 54 genes in Samd2/3 signaling, 48 genes in Wnt-mediated β-catenin signaling, and 44 genes in Notch signaling pathway were identified, respectively (Table 4).

TABLE 4

Predicted targets of miRNAs exhibiting lower than 2-fold expression decrease in recurrent GBM.

| | | Signaling pathways of target genes [b] | | | |
|---|---|---|---|---|---|
| miRNA | Fold change [a] | ErbB1 downstream signaling | Regulation of nuclear Smad2/3 signaling | Wnt-mediated β-catenin signaling and target gene transcription | Notch signaling pathway |
| hsa-miR-9 | 0.35 | ABI1, ARF4, ATF2, DUSP1, DUSP6, JUN, KSR1, MAP2K4, MAP2K5, MAP3K1, RALGDS, RPS6KA4, WASF2 | ATF2, COL1A2, ESR1, FOXG1, FOXO3, JUN, NCOA1, RUNX1, RUNX2, SIN3A, SNIP1 | CTNNB1, JUN, KCNIP4, KLF4, MITF, MYOG, RUVBL2, T, TBL1XR1 | CBL, DLL4, DTXI, EPS15, FURIN, JAG1, MAML2, MIB1, NOTCH2, RBPJ |
| hsa-miR-10b | 0.26 | BCL2L1, MAP3K1, PIK3CA, STAT3, YWHAQ | CDK2, FOXO3, GATA3, IL10, MYOD1, NCOR1, SAP18 | CTNNBIP1, IGF2BP1, YWHAQ | GATA3, MYCBP, NCOR1, NCOR2 |
| hsa-miR-20a* | 0.37 | EGR1, GAB1, KRAS, KSR1, MAP3K1, MAP3K2, MAP3K2, MAPKAP1, | CBFB, CDK2, CDKN1A, E2F5, ESR1, KAT2B, LAMC1, MEF2C, | CAMK4, CCND2, CUL1, HBP1, IGF2BP1, INCENP, MMP2, MYF5, | ADAM12, CDKN1A, CUL1, DLL1, EPS15, FURIN, MIB1, NOTCH2, |

TABLE 4-continued

Predicted targets of miRNAs exhibiting lower than 2-fold expression decrease in recurrent GBM.

| miRNA | Fold change [a] | ErbB1 downstream signaling | Regulation of nuclear Smad2/3 signaling | Wnt-mediated β-catenin signaling and target gene transcription | Notch signaling pathway |
|---|---|---|---|---|---|
| | | MEF2C, PPP2R2A, PRKCA, RPS6KA3, RPS6KA5, SMAD1, STAT1, STAT3, WASF2, WASL, YWHAH, YWHAZ | RBBP7, RBL1, RUNX1, RUNX2, SIN3A, SMAD7, SP3 | NEUROG1, SKP1, SNAI2, T, TBL1X, TCF7, TCF7L1, TLE4, YWHAH, YWHAZ | NOTCH3, RBBP8, RBPJ, SKP1 |
| hsa-miR-95 | 0.24 | CHN2, MAPK9, MEF2C, SMAD1, STAT1, U5P6NL, YWHAH, Z YWHA | CREBBP, GATA3, MEF2C, RBBP7, RUNX1, SMAD2, SMAD4, SP3 | CCND1, CTNNBIP1, TBL1XR1, YWHAH, YWHAZ | ADAM12, CCND1, GATA3, ITCH |
| hsa-miR-105 | 0.01 | ARPC4, CDC42, DUSP6, GRB2, KRAS, MAPKAP1, MEF2C, PIK3R1, PLD1, PRKCA, RAB5A, RALA, RPS6KA5, SMAD1, STAT5, YWHAB, YWHAG | ATF3, CDKN1A, COL1A2, MAX, MEF2C, NCOA1, RUNX1, SNIP1, SP1, SP3 | INCENP, KRT1, LEF1, MDFIC, MITF, TBL1XR1, XPO1, YWHAB, YWHAG | CBL, CDKN1A, ITCH |
| hsa-miR-154 | 0.19 | ABI1, DUSP6, MAP2K5, MAPK3, MEF2C, PIK3R1, PPP2CA, PRKCA, RPS6KA5, WASF2, YWHAG, YWHAZ | CBFB, CREBBP, E2F5, MEF2C, NR3C1, RUNX2, SIN3A, SP1 | BCL9, CCND2, KLF4, YWHAG, YWHAZ | CBL, NOTCH1, NOTCH2 |
| hsa-miR-196a | 0.05 | CALM3, DIAPH3, DUSP6, MAP3K1, NRAS, RALA, RPS6KA3, SH2D2A, STAT1, STAT5, YWHAZ | COL1A2, CREBBP, E2F5, EP300, MAX, SIN3A, SMAD7 | EP300, IGF2BP1, MYF5, MYOG, TLE1, YWHAZ | ADAM10, APH1A, DLL1, EP300, EPS15, MAML1, SPEN |
| hsa-miR-224 | 0.2 | ATF2, CDC42, CREB1, DIAPH3, KSR1, MAP2K4, MEF2C, NRAS, RALA, USP6NL | ATF2, ATF3, CDKN1A, COL1A2, CREB1, CREBBP, MEF2C, RUNX2, SMAD4, SNIP1 | IGF2BP1, MITF, SMARCA4, TBL1XR1, TLE4 | ADAM10, CBL, CDKN1A, DNM1, MIB1, SPEN |
| hsa-miR-299-3p | 0.01 | CDC42, IQGAP1, MAP2K1, MLST8, RAB5A, RPS6KA3 | ATF3, CBFB, KAT2B, SIN3A, SP1, TGIF1 | CAMK4, CUL1, INCENP, KRT1, MMP2, TLE1 | APH1A, CUL1, MARK2, MFAP5, MIB1 |

TABLE 4-continued

Predicted targets of miRNAs exhibiting lower than 2-fold expression decrease in recurrent GBM.

| miRNA | Fold change [a] | Signaling pathways of target genes [b] | | | |
|---|---|---|---|---|---|
| | | ErbB1 downstream signaling | Regulation of nuclear Smad2/3 signaling | Wnt-mediated β-catenin signaling and target gene transcription | Notch signaling pathway |
| hsa-miR-299-5p | 0.09 | CREB1, MAP2K5, MAP2K5, RAC1 | CDKN1A, CREB1, ESR1, FOXG1, SP1 | BTRC, CTNNB1, IGF2BP1, LEF1, TLE1 | ADAM10, BTRC, CDKN1A, DLL4, EPS15, RBPJ |
| hsa-miR-337-5p | 0.01 | BRK1, PPP2CA, RPS6KA3 | ATF3, EP300, IL10 | EP300 | EP300 |
| hsa-miR-376a | 0.18 | ABI1, CREB1, DIAPH3, GRB2, MAP3K1, MAP3K2, NCKAP1, PRKCD, YWHAB | AR, CBFB, CDK2, CDKN1A, CEBPB, CREB1, CREBBP, FOXO4, LAMC1, RBL1, SMAD2, SMAD7, SNIP1, SP1 | AR, IGF2BP1, YWHAB | CDKN1A, EPS15, MFAP5, MIB1, MYCBP |
| hsa-miR-376b | 0.01 | ABI1, CREB1, DIAPH3, GRB2, MAP3K1, MAP3K2, NCKAP1, PRKCD, YWHAB, YWHAH | AR, CBFB, CDK2, CDKN1A, CEBPB, CREB1, CREBBP, FOXO4, LAMC1, RBL1, SMAD2, SMAD7, SP1 | AR, CTNNB1, IGF2BP1, YWHAB, YWHAH | CDKN1A, EPS15, FBXW7, MAML1, MFAP5, MIB1, MYCBP |
| hsa-miR-376c | 0.26 | CREB1, DIAPH3, DUSP6, GRB2, JUN, KRAS, MAP2K4, MAP3K2, MEF2C, RPS6KA4, USP6NL | AR, CREB1, CREBBP, DLX1, HDAC1, JUN, MEF2C, NCOA1, RUNX2, SKIL, SMAD2, SMAD4, SMAD7, SP1 | APC, AR, BCL9, CACNA1G, CCND1, HDAC1, INCENP, JUN, TCF7L1, TLE4 | CCND1, DLL1, FBXW7, HDAC1, MFAP5, MIB1, RBBP8 |
| hsa-miR-379 | 0.24 | ABI1, ELK1, KRAS, MAP3K2, STAT1 | CDKN2B, SAP18, SIN3A, SP1, TFDP1 | XPO1 | APH1A, MAML1 |
| hsa-miR-411 | 0.08 | DUSP1, MAP2K1, MAP3K1, PPP5C | ATF3, CBFB, FOXO1, KAT2B, SAP30, SMAD2 | BCL9, KCNIP4, KLF4, LEF1, MDFIC, SNAI2, TLE4 | ADAM12, ITCH, LNX1 |
| hsa-miR-450a | 0.26 | CDC42, DUSP6, PPP2R2A, PRKCA | FOXG1 | CCND2, TLE1 | FBXW7, MFAP5, MIB1, NOTCH2, NUMB, SPEN |
| hsa-miR-542-3p | 0.29 | BRK1, KRAS, MAP2K4, MAP3K2, MAPKAP1, PIK3R1, PPP2R1A, PRKCA, RAC1, RPS6KA4, SLC9A1, SRC, SRF, WASF2 | AR, ATF3, CDK2, NR3C1, SMAD2, SNIP1, SP1, SP3 | AR, INCENP, MITF, TBL1XR1, TCF7L1, TLE1 | ADAM10, ITCH, MAML1, NCSTN, RAB11A, YY1 |

TABLE 4-continued

Predicted targets of miRNAs exhibiting lower than 2-fold expression decrease in recurrent GBM.

| miRNA | Fold change [a] | ErbB1 downstream signaling | Regulation of nuclear Smad2/3 signaling | Wnt-mediated β-catenin signaling and target gene transcription | Notch signaling pathway |
|---|---|---|---|---|---|
| hsa-miR-542-5p | 0.29 | ELK1, MLST8, STAT1, YWHAB | RUNX2, TCF3 | TLE4, YWHAB | — |
| hsa-miR-571 | 0.01 | MAP2K4, MAPK7, RPS6KA4, STAT1, YWHAE | CDK2, CREBBP, KAT2B, MAX, RUNX2 | CCND2, CDH1, CTNNB1, KCNIP4, MITF, MYOG, TBL1X, TLE4, YWHAE | CNTN1, MFAP5, NOTCH3 |
| hsa-miR-582-5p | 0.22 | CDC42, CHN2, CYFIP2, EPS8, GRB2, IQGAP1, KRAS, MAP2K4, MAP3K1, MAPK9, NCKAP1, PDPK1, PIK3R1, PPP2CA, PRKCA, PRKCZ, RAB5A, RPS6KA3, SMAD1, USP6NL, YWHAE, YWHAZ | CBFB, CREBBP, DLX1, EP300, FOXO1, HDAC2, NCOA1, NR3C1, RUNX2, RUNX3, SAP18, SMAD3, SNIP1, SP1 | APC, BTRC, CCND2, CTNNB1, EP300, HBP1, HDAC2, IGF2BP1, KCNIP4, MITF, SMARCA4, TBL1X, TLE1, XPO1, YWHAE, YWHAZ | ADAM10, ADAM12, APH1A, BTRC, EP300, FBXW7, JAG2, MAML1, MIB1, MYCBP, NOTCH1, NUMB, RBPJ, YY1 |
| hsa-miR-592 | 0.23 | CHN2, CYFIP2, DUSP1, MAP3K2, MEF2C, NCKAP1, PLD1, RAB5A, WASF2, YWHAG | CBFB, CDKN2B, ESR1, FOXO3, IL10, IL5, LAMC1, MEF2C, RUNX1, RUNX2, SIN3A, SIN3B, SMAD7, SP1 | CDH1, CTNNB1, KLF4, MDFIC, MITF, TBL1XR1, YWHAG | ADAM10, ADAM12, CBL, CNTN6, MYCBP |
| hsa-miR-629 | 0.22 | ARPC4, BRK1, GRB2 | CDKN1A, MAX, NR3C1, RUNX2, SMAD2, SNIP1 | BTRC, CCND2, KLF4, LEF1, TCF7L2 | BTRC, CDKN1A, MAML2, MIB1, MYCBP, NOTCH3, YY1 |
| hsa-miR-654-3p | 0.11 | ARF4, ATF2, CDC42, CREB1, FOS, MAPK3, SRF, WASL | ATF2, CDKN1A, CREB1, FOS, KAT2B, NR3C1, RUNX1 | IGF2BP1, INCENP, KCNIP4, TBL1X, TBL1XR1, TLE1 | ADAM10, CDKN1A, ITCH, NOTCH2 |
| hsa-miR-1271 | 0.36 | DUSP6, KRAS, MAP2K1, MAP3K2, MTOR, PPP2R2A, SRF | E2F5, FOXO4, RUNX1, SP1 | CACNA1G, HBP1, IGF2BP1, INCENP, MITF, TBL1XR1 | CBL, MIB1, MYCBP, RAB11A, SPEN, TCTN1 |

[a] Average fold change (recurrent/primary).
[b] Abbreviations are shown in Genbank or Swissprot.

As described above, the present invention provides a composition for diagnosing recurring glioblastoma multiforme and a method for diagnosis using the same. The composition for diagnosing recurring glioblastoma multiforme and the method for diagnosis using the same provide markers capable of diagnosing the occurrence of recurring glioblastoma multiforme, thereby providing data useful for the treatment and prognosis management of recurring glioblastoma multiforme. Furthermore, the markers for diagnosing recurring glioblastoma multiforme can be used in research and development of anti-cancer drugs specific to recurring glioblastoma multiforme.

The invention claimed is:

1. A method of diagnosing and treating recurring glioblastoma multiforme in a subject, the method comprising:
   (a) obtaining a sample brain tissue from the subject and a control brain tissue from a control subject, wherein the control subject has normal glioblastoma multiforme, incipient glioblastoma multiforme, primary glioblastoma multiforme or newly diagnosed glioblastoma multiforme;
   (b) synthesizing a first miR-365 (SEQ ID NO: 1) cDNA and a first miR-450a (SEQ ID NO: 26) cNDA by using the sample brain tissue and a second miR-365 (SEQ ID NO: 1) cDNA and a second miR-450a (SEQ ID NO: 26) cDNA by using the control brain tissue;
   (c) forming a first complex between a first primer specific to miR-365 (SEQ ID NO: 1) and the first or the second miR-365 (SEQ ID NO: 1) cDNAs, and a second complex between a second primer specific to miR-450a (SEQ ID NO: 26) and the first or the second miR-450a (SEQ ID NO: 26) cDNAs;
   (d) detecting that (i) an amount of the first complex from the sample brain tissue is greater than the amount of the first complex from the control brain tissue and (ii) an amount of the second complex from the sample brain tissue is smaller than the amount of the second complex from the control brain tissue, and diagnosing the subject with recurring glioblastoma multiforme; and
   (e) treating the diagnosed subject by conducting at least one of a chemotherapy, a surgery, and a radiation therapy.

2. The method of claim 1, wherein the miR-365 (SEQ ID NO: 1) cDNA is synthesized by using a first PCR primer specific to miR-365 (SEQ ID NO: 1), and the miR-450a (SEQ ID NO: 26) cDNA is synthesized by using a second PCR primer specific to miR-450a (SEQ ID NO: 26).

3. The method of claim 2, wherein the second PCR primer comprises SEQ ID NO: 34.

4. The method of claim 1, wherein the second primer comprises SEQ ID NO: 34.

5. A method of diagnosing and treating recurring glioblastoma multiforme in a subject, the method comprising:
   (a) obtaining a brain tissue sample from a subject; and
   (b) assaying miRNA in the brain tissue sample, detecting that (i) an amount of miRNA of SEQ ID NO: 1 from the brain tissue sample is greater than that of a control sample, and (ii) an amount of miRNA of SEQ ID NO: 26 from the brain tissue sample is smaller than that of the control sample, and diagnosing the subject with recurring glioblastoma multiforme, wherein the control sample is brain tissue obtained from a subject who has normal glioblastoma multiforme, incipient glioblastoma multiforme, primary glioblastoma multiforme or newly diagnosed glioblastoma multiforme; and (c) treating the diagnosed subject by conducting at least one of a chemotherapy, a surgery, and a radiation therapy.

* * * * *